United States Patent [19]

McVay et al.

[11] 4,402,607

[45] Sep. 6, 1983

[54] AUTOMATIC DETECTOR FOR MICROSCOPIC DUST ON LARGE-AREA, OPTICALLY UNPOLISHED SURFACES

[75] Inventors: Lance McVay, Belmont; Pedro Lilienfeld, Lexington, both of Mass.

[73] Assignee: GCA Corporation, Bedford, Mass.

[21] Appl. No.: 150,363

[22] Filed: May 16, 1980

[51] Int. Cl.³ .............................................. G01N 21/01
[52] U.S. Cl. .................................... 356/338; 250/224
[58] Field of Search ............................... 356/337–340, 356/336, 343, 430, 431, 429, 445–448, 335; 250/563, 572, 224

[56] References Cited

U.S. PATENT DOCUMENTS

| 2,755,702 | 7/1956 | Cook | 250/224 |
| 3,176,306 | 3/1965 | Burns | 250/572 |
| 3,526,461 | 9/1970 | Lindahl et al. | 356/337 |
| 4,019,066 | 4/1977 | Lucas et al. | 250/572 |
| 4,103,177 | 7/1978 | Sanford et al. | 356/431 |
| 4,155,012 | 5/1979 | Clarke et al. | 250/563 |

FOREIGN PATENT DOCUMENTS 617188 8/1960 Canada ............................... 356/430

OTHER PUBLICATIONS

Davies, R., "Rapid Response Instrumentation for Particle Size Analysis", A Review Part II, *American Laboratory*, vol. 6, No. 1, pp. 73–86.
NASA Tech. Brief, Fall 1979, "Automatic Inspection of Silicon Wafers".

*Primary Examiner*—Bruce Y. Arnold
*Attorney, Agent, or Firm*—Kenway & Jenney

[57] ABSTRACT

A system for automatically detecting dust or other minute particles on a large-area, optically unpolished surface such as a face of a glass reticle plate used in the production of microelectronic circuits. The system irradiates the surface with a narrow, high intensity beam of monochromatic radiation at a grazing angle, typically ½ degree with respect to the surface. An oscillating mirror scans the beam across the moving surface in a direction generally perpendicular to the direction of plate advance. A beam splitter provides separate inspecting beams for each surface of the plate. Optical systems characterized by a high numerical aperture are positioned on opposite sides of the plate to collect radiation which is scattered from the particles. The optical systems are oriented to accept scattered radiation, and typically have their optical axes at an angle in the range of 60° to 160° measured from the direction of advance. They each utilize a multiplet of cylindrical lenses characterized by excellent resolution and a large numerical aperture, preferably in the range of 0.15 to 0.20. A fiber optic concentrator transmits the scattered radiation from the image plane of the lenses to a detector which generates an electrical signal proportional to the size of the particle. In the preferred form, a comparator circuit with an adjustable threshold level generates a digital signal only when the size of the particle exceeds a predetermined value. Also, the oscillation of the scanning mirror and the advance of the plate provide a timing reference for the particle detection signal to locate the particle on the plate.

27 Claims, 11 Drawing Figures

AUTOMATIC DETECTOR FOR MICROSCOPIC DUST ON LARGE-AREA, OPTICALLY UNPOLISHED SURFACES

BACKGROUND OF THE INVENTION

This invention relates in general to electro-optical scanning systems. More specifically, it relates to a system which uses scattered laser radiation to detect, measure and locate minute dust particles on the surfaces of a reticle plate.

In the manufacture of microelectronic circuits by photolithography, the lay-out of a circuit is frequently first reduced to a physical form as a pattern of dark areas on a photolithographic mask, commonly termed a reticle. The reticle is placed on the stage of a radiation projector to produce an exposure, usually of reduced size, on a wafer which in turn produces a layer of the circuit. It is extremely important that the reticle be free of dust or other particulate matter on both of its surfaces since the dust will be projected as a dark area in the printing of the wafer. The presence of dust on the reticle will often result in an electrical connection or other circuit modification which causes the microelectronic circuit to malfunction. The error will normally not be detected until after a set of wafer chips have been produced. These circuits must be discarded. The economical production of high quality microelectronic circuits is therefore directly related to the ability to detect and eliminate minute dust particles which may be present on the reticle just before it is seated on the optical stage of the projector.

Previously reticles were inspected for dust prior to replacement in the projector by manual inspection in the open air. This procedure has numerous drawbacks. First, a relatively high level of experience and concentration is required of the person inspecting the reticle. Manual inspection is particularly difficult for extremely minute dust particles, for example those having a diameter of approximately 1 to 5 micrometers. Second, if the visual inspection does detect a dust particle, it is difficult to accurately determine its location to remove the particle. Third, because the inspection is performed in an uncontrolled, open-air environment, the reticle can acquire a dust particle after it has been inspected.

Most applications of radiation scattering to the detection or measurement of particles involve the use of forward scattered light from particles suspended in a fluid. However, in a few instances light scattering techniques have been used to examine solid surfaces. For example, J. F. Ready in *Industrial Applications of Lasers* at pp. 331-333 describes several systems for surface inspection using laser light and photodetectors. One system detects the presence of gold nodules on a ceramic surface using light scattered from the nodules. U.S. Pat. No. 3,767,306 describes another system where light is scattered from particles immersed in a thin liquid layer covering the surface. The inspection of a glass surface for the presence of extremely small particles such as dust, however, presents unique problems which are not addressed by these prior art systems. One significant difference is that the surface of the glass reticle is itself comparatively rough and therefore scatters light. This glass induced scattering presents a general background noise which can easily overwhelm the scattering induced by a small dust particle. Another distinction is that dust particles can be extremely small, for example 1 to 5 micrometers in diameter. No known inspection systems utilizing radiation scattering are able to detect particles of this size in a high noise environment.

Another problem unique to the inspection of reticles for dust particles is that it is highly desirable to have a system which is insensitive to particles with dimensions less than some predetermined value. No known system provides a measurement of the particle size, particularly one sensitive enough to distinguish between extremely small particles varying in size by only one or two micrometers. The detection of dust on a reticle is also complicated because the intensity of the scattered radiation varies as a function of both the scattering angle and the particle size so that there is no particular angle which is reliably associated with a maximum or minimum degree of scattering.

It is therefore a principal object of this invention to provide a system for automatically detecting minute particles such as dust on a large-area, flat, and optically unpolished surface, such as a glass reticle plate, with a high degree of reliability.

Another object of the invention is to provide such a system which can be adjusted to detect only particles of at least a predetermined size.

A further object of the invention is to provide a dust particle detection system with the foregoing advantages that also is capable of identifying the location of a detected dust particle on the plate.

Another object is to provide a system with the foregoing advantages that can simultaneously examine both faces of a plate.

Yet another object of the invention is to provide a dust particle detection system with the foregoing advantages which can perform an inspection of a reticle plate immediately before it is seated on the optical stage of a projector.

A still further object of this invention is to provide a system with the foregoing advantages that can be used in a controlled atmosphere to reduce the likelihood of contamination of the plate following the inspection.

SUMMARY OF THE INVENTION

An automatic system for detecting microscopic particles such as dust on a generally large-area, flat, optically unpolished surface such as a face of a reticle plate includes a laser and associated optical elements that direct a high intensity, narrow beam of radiation onto the surface under investigation at an extremely acute angle, preferably a grazing angle of approximately ½ degree, measured from the surface. The plate is advanced in a "longitudinal" direction coplanar with the plate surface under investigation. In the preferred form an oscillating mirror or an equivalent structure scans the irradiating beam across the plate in a direction generally transverse to the direction of advance. The optical elements directing the beam from the laser to the plate preferably include a beam splitter which divides the beam into two beams of substantially equal intensity that irradiate opposite faces of the plate.

An optical system collects scattered radiation from dust particles located on each face of the plate. In the preferred form, the optical system is a multiplet of cylindrical lenses with their optical axis disposed at an angular orientation in the range of 60° to 160° measured from the direction of advance. The lens system is characterized by a large numerical aperture, preferably in the range of 0.15 to 0.20, and a high degree of resolution at the face of the reticle, in order to minimize the surface scattering background signal associated with a large field of view. In other terms, the lens system accepts a cone of scattered radiation generated at a particle with a conical half angle of approximately 10° (for focused rays). The grazing angle of incidence of the beam together with this optical collecting system yield a good signal-to-noise ratio.

The longitudinal axes of the cylindrical lenses are aligned with a generally rectangular field of view on the plate. The cylindrical lenses focus the scattered radiation on a fiber optic concentrator formed by a bundle of optical fibers. The light receiving ends of the fibers are arranged in a generally rectangular "line" configuration at the image plane of the cylindrical lens system. The fibers are preferably randomly oriented. Their output ends are closely packed in a "spot" pattern that directs the collected radiation to a detector. The detector generates an electrical signal proportional to the intensity of the radiation incident on it from the fiber optic concentrator. Enhanced scattering due to the presence of a dust particle on the plate surface results in an increase in the intensity of the scattered radiation, and hence an increase in the amplitude of the electrical signal produced by the detector. The signal is approximately proportional to the cross-sectional area of the dust particle inducing the scattering. Also in preferred form the system includes electronic sensing circuitry which responds only to electrical signals from the detector of at least a predetermined value thereby providing automatic discrimination in the size of the dust particles to which the system will respond. The circuitry can also correlate the advance of the plate and the beam scan with the output signal of the detector to locate a detected particle on the plate.

These and other features and objects of this invention will be more fully understood from the following detailed description of the preferred embodiments of the invention which should be read in light of the accompanying drawings.

DETAILED DESCRIPTION OF THE PREFERRED EMBODIMENTS

Figure 1:
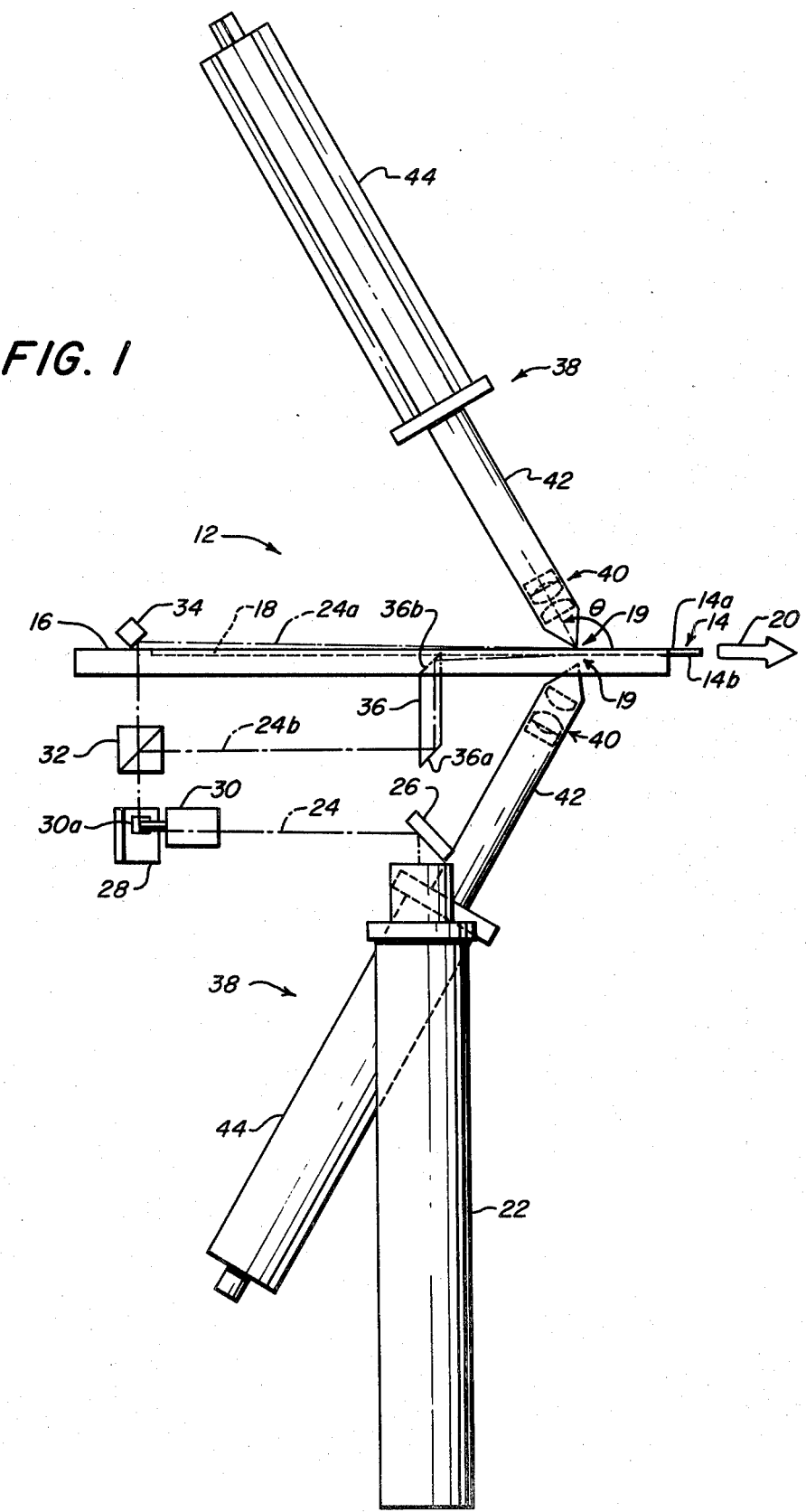
FIG. 1 is a simplified view in side elevation of an automatic dust detection system according to the present invention.
Figure 2:
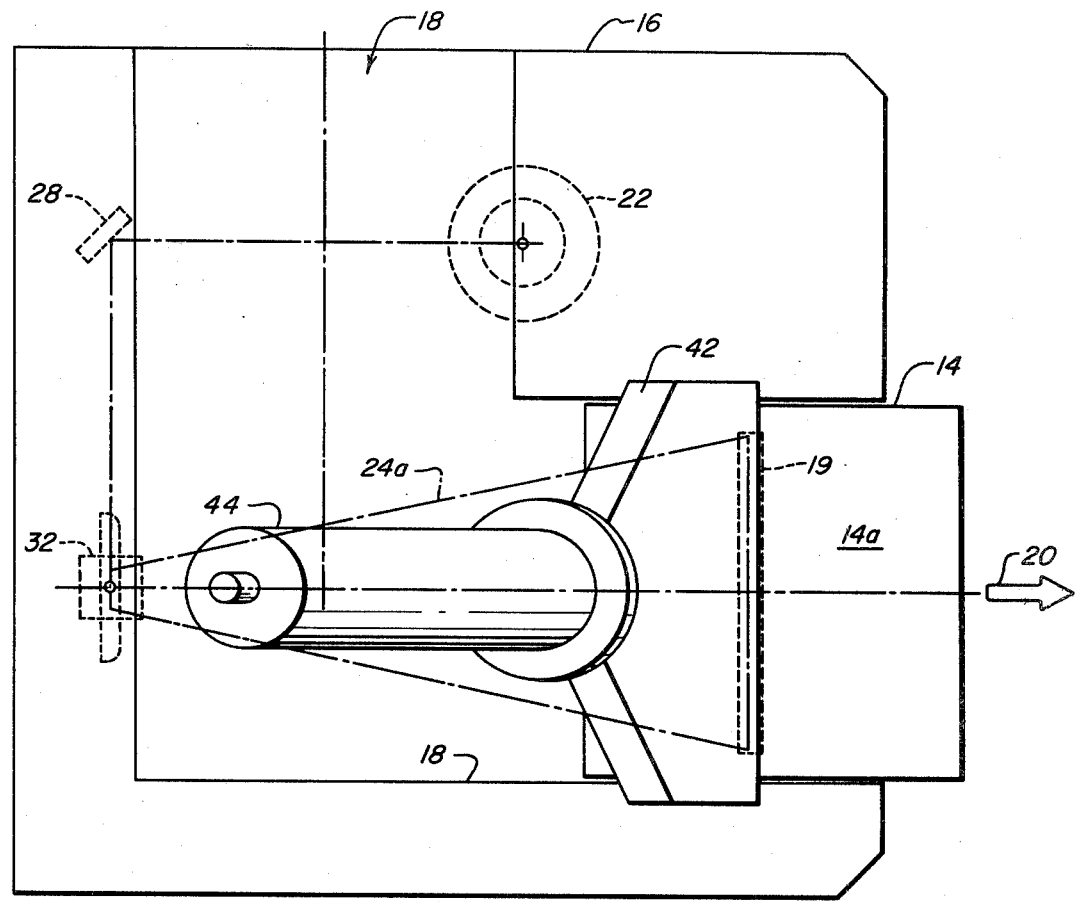
FIG. 2 is a top plan view of the detection system shown in FIG. 1.
Figure 3:
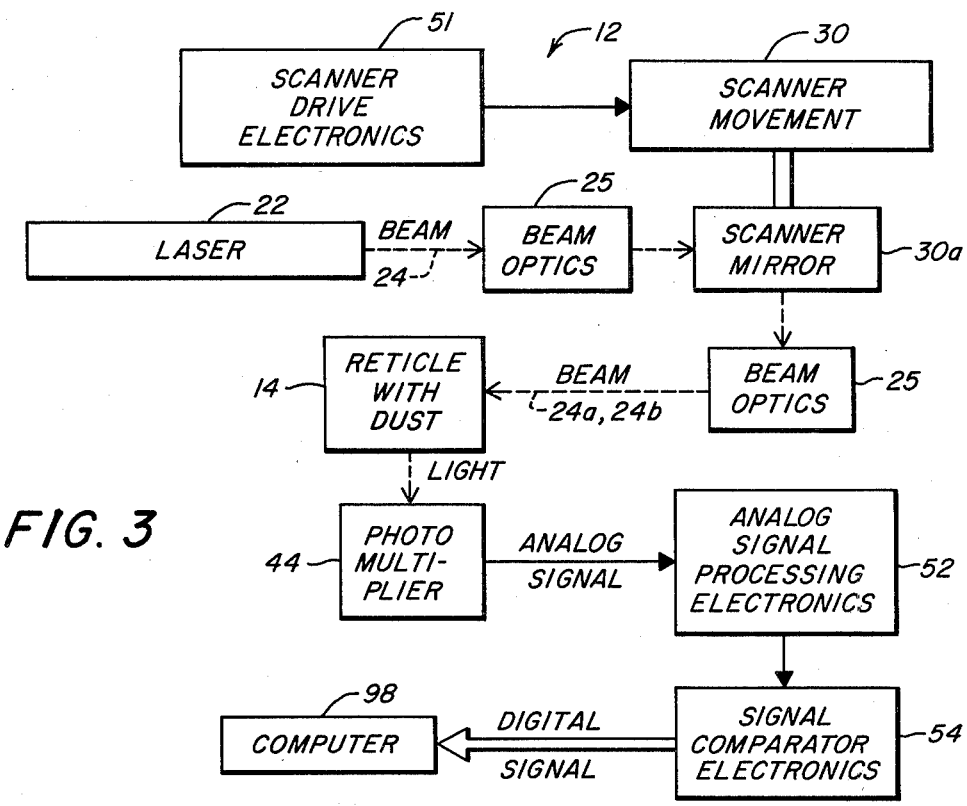
FIG. 3 is a schematic block diagram of the detection system shown in FIGS. 1 and 2 including the associated electronic circuitry.

FIGS. 1–3 show a system 12 according to the present invention for automatically detecting minute particles such as dust resting on a relatively large-area, flat surface. The system is particularly useful in inspecting a glass photographic plate 14, commonly termed a reticle, used in the production of microelectronic circuits. The reticle carries a pattern of dark areas formed by a thin (e.g. 0.6 micrometer) layer of chrome deposited on one of its faces. Typical dimensions for a reticle are 127 mm × 127 mm × 2.29 mm. The projection image area of this reticle, which includes the chrome pattern, is approximately 105 mm square. An important feature of the reticle is that the glass face themselves as well as the dark chrome pattern will scatter light.

The detection system 12 includes an air plate 16 with a channel or track 18 formed in its upper surface. The track 18 guides the reticle 14 through the detection system and onto the optical stage of a step-and-repeat projector (not shown) where the reticle is used to expose a wafer. Air nozzles (not shown) mounted in the plate 16 provide both an air bearing and propulsion for the reticle as it moves through the channel 18. The velocity of the reticle advance is substantially constant. An arrow 20 indicates the direction of advance of the reticle from the track 18 onto the optical stage. A significant advantage of the present invention is that the reticle is inspected for the presence of dust particles at a point very near the center of the optical stage, a representative value being six inches.

Each face of the reticle is irradiated over a generally rectangular scanning region by a narrow, high intensity beam 24 of monochromatic radiation. This beam is preferably generated by a laser 22 and can have a wavelength of, for example, 630 nm (visible light). The beam is characterized by a small angular divergence, and preferably has a width at the scanning region 19 of approximately 0.5 mm or less measured between the half maxima of the beam intensity profile. The high intensity of the beam is important to provide a good signal to noise ratio when it is scattered from a dust particle located on an upper face 14a or lower face 14b of the reticle 14. A recommended value for the beam intensity is 0.1 W/mm$^2$.

Optical elements which direct the beam 24 from the laser 22 to the reticle scanning region including a first folding mirror 26, a second folding mirror 28, an optical scanner 30 including an oscillating scanning mirror 30a, a beam splitter 32, a third folding mirror 34, and a double reflecting prism 36. The mirror 26 directs the beam from an upward direction as it exits the laser to a horizontal orientation toward the second mirror 28 which in turn reflects the beam horizontally onto the scanning mirror 30a of the optical scanner 30. The scanning mirror 30a is inclined at a 45° angle with respect to the horizontal plane of the beam path determined by the mirrors 26 and 28 to direct the beam upwardly to the beam splitter 32. The scanner mirror oscillates in a manner which scans the beam in a fan-like manner as is best seen in FIG. 2. The beam splitter 32 is preferably a conventional cubic splitter that divides the incident beam into an upper scanning beam 24a and a lower scanning beam 24b of substantially equal intensity. The beam 24a proceeds upwardly through an aperture in the plate 16 to the third folding mirror 34 which directs the beam onto the upper face 14a of the reticle. The lower beam 24b, reflected by the beam splitter 32, proceeds along a substantially horizontal path to the prism 36 where it is internally reflected twice at faces 36a and 36b emerging from the prism 36 onto the lower face 14b of the reticle.

While these beam optics (denoted generally in FIG. 3 by reference numeral 25) can vary widely as to their constituent elements and the beam geometry, a principal feature of this invention is that the narrow, high intensity scanning beams 24a and 24b each strike the faces of the reticle at an extremely small angle measured from the surface under inspection. This inspection angle has been found to be extremely important in providing a good signal to noise ratio in the detection of small particles in a high noise background. More specifically, the system 12 is designed to detect dust particles having a diameter as small as 1 to 5 micrometers. In prior art scanning systems where the interrogating light is directed onto the surface at a much larger angle of incidence, the noise level generated by light scattered from the surface itself would overwhelm the signal generated by the light scattered from small dust particles resting on the surface.

The optical scanner 30, which can be the unit sold by General Scanning, Inc. under the trade designation Model No. G115, has a mirror 30a which oscillates at a frequency of approximately 50 Hz. The amplitude of the oscillation is sufficient to scan the beam laterally in a direction generally perpendicular to the direction of advance 20 of the reticle over the projection image area which will be photolithographically reproduced. For a typical 127 mm square reticle, the beam therefore scans laterally over the reticle for a distance of approximately 105 mm. Because of the grazing angle of inspection of the beam, the beam irradiates a face area of the reticle extending longitudinally (in the direction 20) for approximately two inches with the precise length depending on the inspection angle and the beam width. This irradiated area is the scanning region of the faces 14a and 14b.

The beam splitter 32 is spaced from the lower face of the plate 16 so that the lower split beam 24b reflected from the beam splitter to the prism 36 avoids air bearing components (not shown) located under the plate. The prism 36 provides a "dog leg" in the beam path that elevates the beam 24b so that it is horizontal and directed onto the reticle face 14b at the aforementioned grazing angle. It should also be noted that because the beam is fanned by the scanner mirror before it enters the splitter 32, both the upper and lower split beams 24a and 24b are scanned laterally across the reticle.

A pair of electro-optical light collecting assemblies 38, 38 are arranged symmetrically about the scanning regions on opposite sides of the reticle 14. Each assembly 38 includes an optical light collecting and relay system, preferably a multiplet of cylindrical lenses 40, which have excellent resolution in the scanning regions and a large numerical aperture. In the preferred form shown, each multiplet 40 is a triplet as shown in detail in FIGS. 4 and 5. Preferably the lens system 40 is capable of resolving narrow fields of view 19, 19 lying in the scanning regions of the faces 14a and 14b. The fields of view 19, 19 each extend laterally over the projection image area on the reticle surface (typically 105 mm) and longitudinally for approximately 0.5 mm. This lens system collects and relays scattered light from a detecting region 19, 19 to a generally rectangular image plane. Fiber optic concentrator assemblies 42, 42 each transmit the collected light from the image plane to a photomultiplier tube 44.

Another significant feature of this invention is that the lens systems 40, 40 have their principal optical axes aligned with respect to the associated field of view 19 at an angle that enhances the signal-to-noise ratio. The systems 38, 38 preferably collect light scattered at an angle $\theta$ with respect to the forward direction of motion of the reticle having a value in the range of 60° to 160°. More specifically, it has been found that a collecting angle of about 120°, as shown, significantly enhances the signal-to-noise ratio for minute dust particles scattered from the glass reticle surface.

Figure 11:
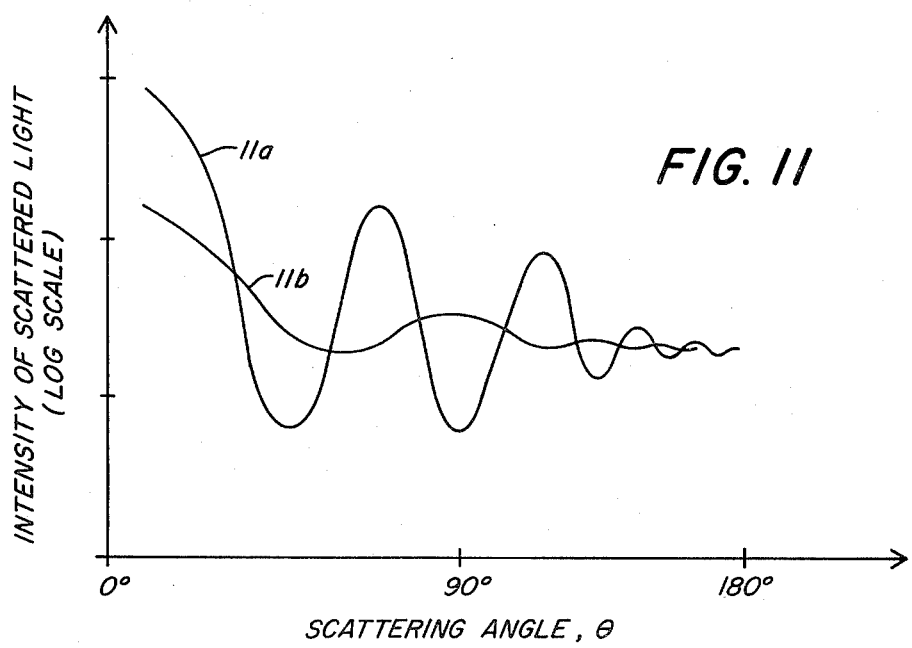
FIG. 11 is a graph of the intensity of light scattered from a particle as a function of the scattering angle.

Another principal feature of the invention is that each cylindrical lens triplet 40 is characterized by a large numerical aperture, preferably one in the range of 0.15 to 0.20. Stated in other terms, the cylindrical lens systems 40, 40 when viewed from a particle in one field of view 19 subtend a conical half angle of approximately 10° for focused rays. This large numerical aperture is important to integrate the light collection over a fairly large annular domain in the object space. The importance of this large numerical aperture is best understood with reference to FIG. 11 which gives a typical graph of scattered light intensity from two small particles as a function of the scattering angle $\theta$ where 0° represents completely forward scattered light and 180° represents completely back scattered light. Graph 11a demonstrates a typically intensity pattern for a comparatively large particle. Graph 11b shows a comparable pattern for light scattered from a substantially smaller particle. In general, with smaller particles the variation of the intensity with the angle has a lower frequency and a smaller amplitude. But in either case, if a system collects light at only one scattering angle, the detection angle may coincide with a minimum of the intensity pattern and therefore the particle may avoid detection. However, if the scattered light is collected over a range of angles, then fluctuations in the intensity due to variations of the scattering angle are averaged out. It is also important that the lenses 40 collect light from an exceptionally large (105 mm wide) field of view, even though the "instantaneous" field of view illuminated by the narrow beam at any moment in time is significantly smaller. This large field of view is provided in part by the use of cylindrical lenses.

Figure 4:
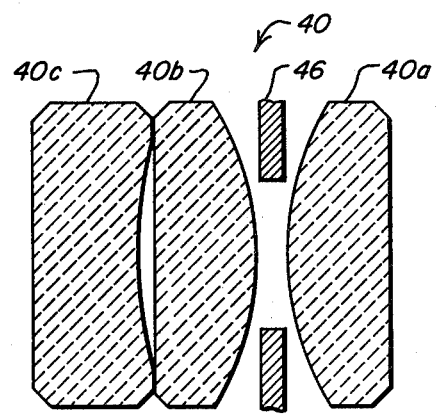
FIG. 4 is a detail view in side elevation of the cylindrical lens triplet shown in FIGS. 1 and 2 and used to collect particle scattered light.
Figure 5:
FIG. 5 is a view in front elevation of the first element of the triplet shown in FIG. 4.

With reference to FIGS. 4 and 5, each cylindrical lens triplet 40 includes a first lens element 40a, a second lens element 40b, and a third lens element 40c with an aperture stop 46 located between the first and second elements. Each of the lenses 40a, 40b, and 40c is cylindrical and has a longitudinal axis which preferably extends at least the width of the field of view 19 and preferably extends beyond both the lateral ends of the associated field of view 19 a sufficient distance to subtend a conical half angle of 10° when viewed from a point at the edge of the reticle image area. By way of illustration but not of limitation, the lens elements 40a, 40b, and 40c are preferably formed of glass having an index of refraction of approximately 2.44. Each lens element has a length, measured along its longitudinal axis, of approximately 135 mm and a height of approximately 10 mm. The first lens 40a is a converging element with a planar first surface and a second surface with the radius of curvature of 8.91 mm. The lens 40b, also converging, is spaced from the element 40a by 1 mm. The lens 40b has a convexly curved first surface with a radius of curvature of approximately 8.91 mm and a planar second surface. The lens 40c is a diverging element having a concave first surface with a radius of curvature of 14.21 mm and a planar second surface. The perpheries of the second and third elements are in contact. The first surface of the lens 40a is disposed approximately 13 mm from the field of view 19. Each of the lenses 40a, 40b, and 40c have a maximum thickness measured along the principal optical axis of approximately 3.5 mm. The lens system 40 has an image plane located approximately 9.15 mm behond the second surface of the lens 40c.

Figure 7:
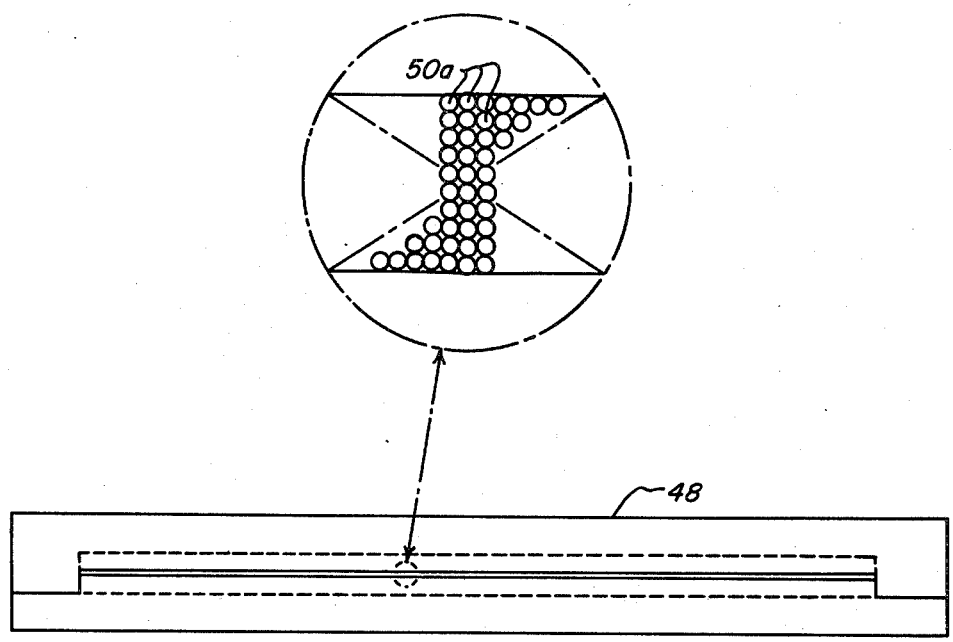
FIG. 7 is a view of the light concentrator shown in FIG. 6 taken along the line 7—7.
Figure 6:
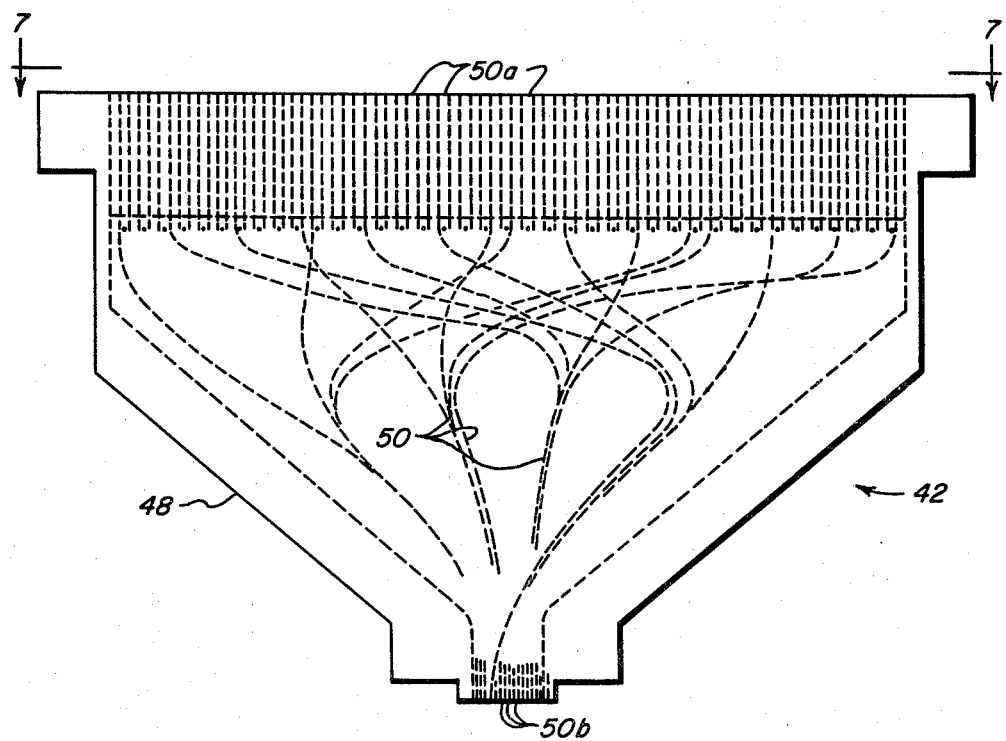
FIG. 6 is a top plan view of the fiber optic light concentrator assembly shown in FIGS. 1 and 2.

Each fiber optic concentrator assembly 42 includes a generally fan shaped housing 48 which encloses a mass of fine optical fibers 50 each having a first end 50a (as best seen in FIG. 7) lying in the image plane of the cylindrical lens triplet 40 and adapted to receive the scattered light collected by the lens. Each of the fibers 50 are clad to efficiently transmit the light collected at its end 50a to an output end 50b. The fiber ends 50a are generally arrayed along a line extending the length of the cylindrical lens triplet and extending vertically for a sufficient distance to collect and transmit along the fibers 50 substantially all of the light incident upon the associated lens system 40. In the preferred form, the fibers have a diameter of approximately 0.05 mm and are stacked approximately 10 deep at their input ends 50a (see detail in FIG. 7). The fibers are preferably randomly oriented and grouped into four or five bundles before they are secured into a tightly packed, "spot" light emitting configuration which irradiates the cathode of the photomultiplier tube 44. Adjacent fibers ends 50a or 50b are generally parallel and square with respect to the axis of the fiber. The assembly 42 provides an efficient device for a "line to spot" transformation of the light output of the associated lens system 40.

Referring to FIG. 3, the detection system 12 also includes various electronic components such as a scanner drive circuit 51, an analog signal processing circuit 52, and signal comparator circuit 54. The circuit 51 generates an output signal which drives the scanner 30 at the desired frequency and amplitude of oscillation. The circuit 51 also generates a logic signal output 72. A microcomputer 98 uses this logic signal to yield the location of the scanner mirror, and hence the lateral position of the scanning beam, as a function of time. Each photomultiplier 44 converts the light incident upon it from the output ends 50b of the light concentrator assembly into an analog electrical signal which is substantially proportional to the intensity of the light. The analog signal processing circuit 52 converts this analog signal from the photomultiplier into a voltage signal suitable for evaluation by the signal comparator circuit 54.

The comparator circuit 54 has at least one and preferably four adjustable and predetermined voltage levels each of which corresponds to a given particle size. Depending on whether or not the signal exceeds a predetermined level, the signal comparator produces a digital signal output which indicates the presence or absence of a particle of that size. This digital signal can be applied to any of a variety of signalling devices, but preferably is applied to the minicomputer 98 which, in addition to controlling a suitable signalling device, also correlates the presence of a particle with the logic output of the circuit 51 to determine the lateral position of the particle on the reticle. Information concerning the longitudinal position of a detected particle is determined from signals generated by the leading and trailing edges of the reticle as it passes through the detection system. More specifically, these edges generate extremely large degrees of back scattered light which the system 12 interprets as an extremely large number of particles present in a single scan. This "many particles" situation is interpreted by the computer as one of the edges. Since the reticle is advancing at a constant speed, and the time its leading and trailing edges pass under the detection system are known, the longitudinal position of a particle is readily calculated.

Figure 8:
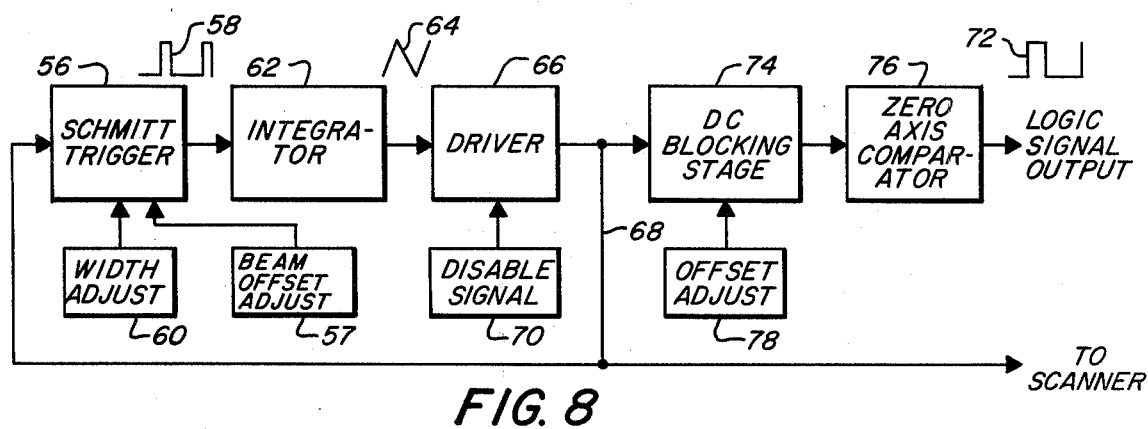
FIG. 8 is a block diagram of the drive circuit for the scanning mirror shown in FIGS. 1 and 2.

FIG. 8 is a simplified block diagram of the electronic circuit 51 for the scanner drive. A Schmitt trigger circuit 56 generates a square wave output signal 58. A width adjustment circuit 60 allows adjustment of the duration of the pulse outputs of the Schmitt trigger 56. The output signal 58 is applied to an integrator 62 which produces an output signal 64 with a sawtooth waveform. This signal is then applied to a driver 66 which is essentially a power amplifier that increases the strength of the signal. The output of the driver is applied over line 68 to the scanner 30. The lateral sweep width is thus controlled by the width adjustment 60 and may be displaced by an offset adjustment 57. A disable signal circuit 70 provides an electronic on/off control for the driver 66. This allows a convenient method for stopping the scanner 30. This is desirable for example, when the reticle reaches the optical projection stage since vibrations generated by the scanner motor may interfere with the lithographic processes.

The logic signal output 72 turns "true" (0V) when the lateral sweep of the beam first enters the projection image area and turns "false" (+5 V) when the beam first leaves the image area. This logic signal is generated by passing the scanner signal 68 through a DC blocking stage 74 and a zero axis comparator 76. Whenever the scanner signal is greater than zero volts, the comparator 76 generates a "true" logic signal. The logic signal 72 transition from "false" to "true" is set to coincide with the lateral sweep of the beam first entering the image area by aligning an offset adjustment 78.

Figure 9:
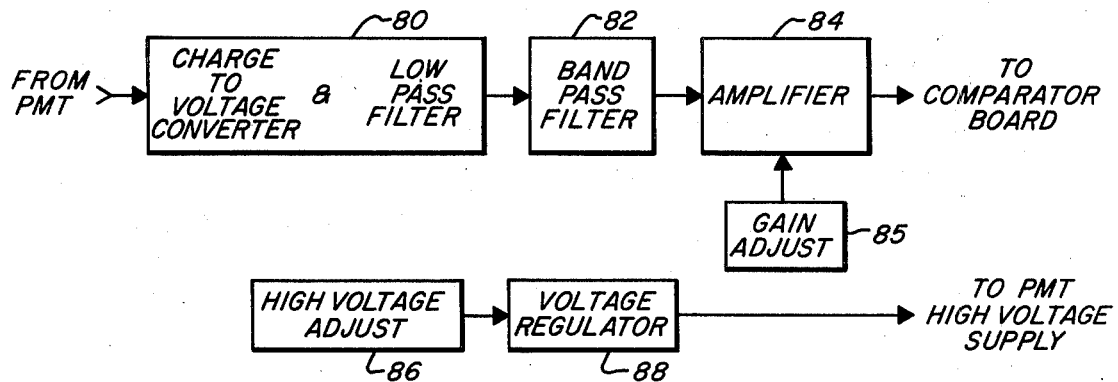
FIG. 9 is block diagram of the circuit that processes the signal from one of the photomultiplier tubes shown in FIGS. 1 and 2 and a high voltage supply for the tube.

FIG. 9 shows in more detail the analog signal processing circuit 52 associated with one of the light collecting assemblies 38. The circuit 52 therefore has two independent circuits of the type shown in FIG. 9, each associated with one of the assemblies 38. The output signal of the photomultiplier tube 44 is applied to a charge-to-voltage converter and low pass filter network 80. The low pass filter eliminates very high frequency noise from the output voltage signal of the photomultiplier. The output signal of the network 80 is then applied to a band pass filter 82 which filters out all signals that do not fall within a predetermined range of signal pulse widths. The output of the band pass filter 82 is then applied to an amplifier 84 with a gain control 85. The signal processing electronics also includes a high voltage adjustment 86 and a voltage regulator 88 which controls the input voltage to the high voltage supply for the associated photomultiplier tube.

Figure 10:
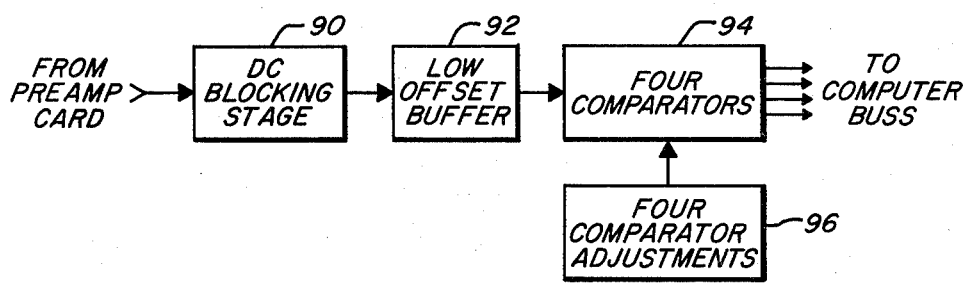
FIG. 10 is a block diagram of the circuit for comparing the output signal of one of the photomultiplier tubes to a predetermined signal values corresponding to a known particle sizes.

FIG. 10 shows in more detail one half of the signal comparator circuit 54 associated with one of the detector assemblies 38. The output signal of the amplifier 84 is applied to a DC blocking stage 90 and a low offset buffer 92 which prevents the output voltage from becoming sufficiently negative to adversely affect the performance of a following comparator circuit 94. The output of the buffer is preferably applied to four comparators each of which compares the analog output signal of the photomultiplier tube to a predetermined voltage level which corresponds to a predetermined particle size. A comparator adjustor 96 for each of the four comparators sets these four threshold or discrimination levels. Typical values for these thresholds correspond to particles having diameters of five, ten, twenty and forty micrometers. The existence of several comparators provides immediate information as to particle size as well as information as to whether or not a particle of sufficient size to trigger the lowest value comparator is present. The output of the four comparators is a digital signal which is applied to a bus for the minicomputer 98. The minicomputer can in turn provide a variety of control and processing functions such as initiating a signal to activate an alarm device or counter, or correlating the presence of a particle with the logic signal output of the scanner circuit to give an indication of the lateral position of a detected particle on the reticle. If, as discussed above, the minicomputer is also programmed to interpret a reading of a large number of particles in a single scan as a leading or trailing edge of the reticle, it can also calculate an approximate longitudinal position for the particle on the reticle. As will be well understood by those skilled in the art, the minicomputer can also perform more sophisticated functions such as a particle size distribution analysis.

There has been described a highly reliable system for detecting extremely small dust particles resting on a large area surface that is itself light scattering. The system is automatic and not only detects particles in excess of one or more predetermined sizes, but can also provide information as to the location of a detected particle on the surface. The system allows an inspection of a reticle at a point very close to the optical stage of a step and repeat projector. Also, the entire detection area and optical exposure area can be maintained in a controlled environment such as a vacuum or a clean atmosphere of a highly filtered gas.

While the invention has been described with respect to its preferred embodiments, it will be understood that the function of various components of this system can be achieved in a variety of ways well known to those skilled in the art. For example, the beam optics which control the transmission of the radiation beam from the laser to the reticle plate can be widely altered with, for example, two lasers each of which is associated with the inspection of one face of the plate or the inspecting beam of radiation oriented in a direction transverse to the direction of advance of the plate. With this latter arrangement, the detector assemblies 38, 38 can be scanned over the field of view rather than the beam. One conventional arrangement for scanning the field of view is a movable aperture placed before the lens system 40. Similarly those skilled in the art will readily be able to design a variety of electronic circuits for driving a scanning mirror or processing and evaluating the output signal of the photomultiplier tube.

Further, while the invention has been described with reference to an inspecting beam of radiation that is in unpolarized, in certain applications it may be possible to achieve a better signal-to-noise ratio by either using polarized incident radiation, by collecting only one polarization of scattered radiation (by means of a polarizer), or both. Also, each particle on the plate can be scanned several times, each time with a different polarization geometry, using conventional electro-optic polarization components.

These and other modifications and alterations of the invention will become apparent to those skilled in the art from the foregoing detailed description and the accompanying drawings. Such modifications are intended to fall within the scope of the impended claims.

What is claimed as new and secured by Letters Patent is:

1. A system for detecting the presence of microscopic particulate matter on a generally flat, large area and optically unpolished surface with randomly oriented surface irregularities, said surface advancing in a first direction that is generally coplanar with the surface, comprising, means for generating a narrow beam of high intensity monochromatic radiation, means for directing the radiation onto said surface at a highly acute angle measured from said surface, said radiation being scattered by said particulate matter and said optically unpolished surface, said surface scattered radiation having a random orientation with respect to said radiation generating means and a frequency spectrum similar to the frequency spectrum generated by said radiation scattered by said particulate matter to thereby create a background noise, optical means angularly oriented with respect to said surface to collect radiation from said beam that is scattered by said particulate matter and from said optically unpolished surface, said optical means having high resolution in the field of view on said surface and a large numerical aperture, said particle scattered radiation received by said optical means being generally proportional to the size of said particulate matter, electronic means operatively coupled to said optical means for converting said particulate matter scattered radiation into an analog electrical signal whose amplitude corresponds to the intensity of said collected radiation, and electronic means for filtering out from said signal noise due to scattering of said radiation from said surface.

2. The system of claim 1 further comprising means for scanning said beam laterally across said field of view in a direction generally transverse to said first direction.

3. The system of claim 2 wherein said optical means includes a multiplet of cylindrical lenses with their longitudinal axes generally aligned with said scanning direction.

4. The system of claim 3 wherein said eletronic means for inverting comprises a photomultiplier tube.

5. The system of claim 4 wherein said optical means further includes a fiber optic light guide that transmits light from the image plane of said lenses to said photomultiplier tube.

6. The system of claim 2 further comprising means for coordinating said scanning means and said electronic means for converting to determine the location of said particulate matter on said surface.

7. The system of claim 6 wherein said means for coordinating includes electronic means for interpreting an increased intensity of the scattered radiation from an edge of the surface in a single scan as the leading or trailing edge of the surface.

8. The system of claim 1 wherein said electronic means for filtering comprises means for converting said analog signal into a digital signal.

9. The system of claim 8 wherein said analog-to-digital converting means comprises a comparator.

10. The system of claim 1 wherein said optical means can resolve particulate matter in said field of view having a diameter in the range of 1 to 5 micrometers and said optical means has a numerical aperture in the range of 0.15 to 0.20.

11. The system of claim 1 wherein said said optical means is angled to collect radiation emanating in the directions of from 60° to 160° measured from said first direction.

12. The system of claim 1 wherein said highly acute angle is approximately ½ degree.

13. The system of claim 1 further comprising means for splitting said radiation beam into two separate scanning beams which are each directed at opposite sides of said surface at said highly acute angle.

14. The system of claim 1 wherein said narrow beam of high intensity monochromatic radiation is polarized to enhance the signal-to-noise ratio of said particle scattered radiation to said surface scattered radiation.

15. A system for automatically detecting very small particles of at least a predetermined size on either of two generally parallel faces of a reticle that is advancing in a first direction that is generally coplanar with the faces comprising:
   a laser light source that generates a narrow beam of high intensity monochromatic light having a small angular divergence,
   means for splitting said beam into two beams of generally equal intensity,
   means for directing each of said split beams onto a scanning region of an associated one of said faces at a highly acute angle measured from said faces,
   means for scanning each of said split beams laterally across said scanning region in a direction generally transverse to said first direction, and
   optical means angularly oriented with respect to said faces to collect light from said split beams that is scattered from said particles lying in a field of view within said scanning regions, said optical means having high resolution for said fields of view and a large numerical aperture,
   said particle scattered light received by said optical means being generally proportional to the size of said particulate matter.

16. The system of claim 15 wherein the angular orientation of said optical means is in the range of 60° to 160° measured from said first direction.

17. The system of claim 15 wherein said numerical aperture is in the range of 0.15 to 0.20 and said optical means can resolve adjacent particles in said fields of view having a diameter in the range of 1 to 5 micrometers.

18. The system of claim 15 further comprising means operatively coupled to said optical means for converting said particulate matter scattered light into an electrical signal whose amplitude corresponds to the intensity of said collected light.

19. The system of claim 18 wherein said converting means comprises a photomultiplier tube.

20. The system of claim 19 wherein said optical means includes a multiplet of cylindrical lenses with their longitudinal axes generally aligned with said scanning direction.

21. The system of claim 20 wherein said optical means further includes a fiber optic light guide that transmits light from the image plane of said lenses to said photomultiplier.

22. The system of claim 18 further comprising electronic comparator means responsive to said electrical signal.

23. The system of claim 18 further comprising means for coordinating said scanning means and said converting means to locate said particulate matter on said surface.

24. The system of claim 15 wherein said light is polarized.

25. The system of claim 15 wherein said optical means includes means for detecting scattered radiation having a predetermined polarization.

26. The system of claim 15 wherein said optical means has a large field of view in said scanning direction.

27. The system of claim 15 wherein said narrow beam of high intensity monochromatic light is polarized to enhance the signal-to-noise ratio of said particle scattered light to light scattered from said reticle.

* * * * *